(12) United States Patent
Dowlatshahi (10) Patent No.: US 8,486,127 B2
(45) Date of Patent: Jul. 16, 2013

(54) HIGH TEMPERATURE THERMAL THERAPY OF BREAST CANCER

(75) Inventor: Kambiz Dowlatshahi, Chicago, IL (US)

(73) Assignee: Kambiz Dowlatshahi, Chicago, IL (US)

( * ) Notice: Subject to any disclaimer, the term of this patent is extended or adjusted under 35 U.S.C. 154(b) by 1056 days.

(21) Appl. No.: 11/753,510

(22) Filed: May 24, 2007

(65) Prior Publication Data

US 2007/0288075 A1   Dec. 13, 2007

Related U.S. Application Data (60) Provisional application No. 60/808,064, filed on May 24, 2006, provisional application No. 60/915,852, filed on May 3, 2007.

(51) Int. Cl.
*A61F 7/12* (2006.01)

(52) U.S. Cl.
USPC .......................................................... 607/105

(58) Field of Classification Search
USPC .......................................................... 607/105
See application file for complete search history.

(56) References Cited

U.S. PATENT DOCUMENTS

| | | | | |
|---|---|---|---|---|
| 4,323,056 A | * | 4/1982 | Borrelli et al. | 600/10 |
| RE32,066 E | * | 1/1986 | Leveen | 607/154 |
| 4,908,014 A | * | 3/1990 | Kroyer | 604/6.13 |
| 4,955,377 A | * | 9/1990 | Lennox et al. | 607/105 |
| 5,092,841 A | * | 3/1992 | Spears | 604/103.01 |
| 5,099,756 A | * | 3/1992 | Franconi et al. | 600/10 |
| 5,106,360 A | * | 4/1992 | Ishiwara et al. | 600/2 |
| 5,429,582 A | * | 7/1995 | Williams | 600/2 |
| 5,431,648 A | * | 7/1995 | Lev | 606/27 |
| 5,931,774 A | * | 8/1999 | Williams et al. | 600/2 |
| 6,383,151 B1 | * | 5/2002 | Diederich et al. | 601/2 |
| 6,516,211 B1 | * | 2/2003 | Acker et al. | 600/411 |
| 6,623,453 B1 | * | 9/2003 | Guibert et al. | 604/103.01 |
| 6,923,754 B2 | * | 8/2005 | Lubock | 600/3 |
| 2002/0082556 A1 | * | 6/2002 | Cioanta et al. | 604/113 |
| 2002/0183620 A1 | * | 12/2002 | Tearney et al. | 600/473 |
| 2004/0147811 A1 | * | 7/2004 | Diederich et al. | 600/207 |
| 2005/0124843 A1 | * | 6/2005 | Singh | 600/3 |
| 2005/0171525 A1 | * | 8/2005 | Rioux et al. | 606/41 |
| 2005/0261670 A1 | * | 11/2005 | Weber et al. | 606/21 |
| 2006/0118127 A1 | * | 6/2006 | Chinn | 128/898 |
| 2006/0126789 A1 | * | 6/2006 | Dinsmore et al. | 378/121 |
| 2006/0173388 A1 | * | 8/2006 | Ginter et al. | 601/3 |
| 2006/0178666 A1 | * | 8/2006 | Cosman et al. | 606/41 |
| 2006/0282039 A1 | * | 12/2006 | Duong et al. | 604/113 |
| 2007/0149963 A1 | * | 6/2007 | Matsukuma et al. | 606/28 |

(Continued)

OTHER PUBLICATIONS

International Search Report issued in PCT/US2007/69691 (2007).

(Continued)

*Primary Examiner* — Linda Dvorak
*Assistant Examiner* — Kaitlyn Smith
(74) *Attorney, Agent, or Firm* — Barnes & Thornburg LLP; Alice O. Martin (57) ABSTRACT

A method is described for preventing breast cancer recurrence after surgical removal of a breast cancer mass. Specifically, the method is thermal treatment of breast tissue surrounding a cavity after lumpectomy for breast cancer. Delivery of a heated fluid is through a balloon catheter to the cavity generated after lumpectomy with the goal of ablating the surrounding tissue, including transformed cells that were not removed through surgery. A balloon and controller were designed for this application.

2 Claims, 7 Drawing Sheets

U.S. PATENT DOCUMENTS

| | | | |
|---|---|---|---|
| 2008/0021305 A1* | 1/2008 | He et al. | 600/411 |
| 2008/0223380 A1* | 9/2008 | Chinn | 128/898 |
| 2008/0264423 A1* | 10/2008 | Duchon et al. | 128/830 |
| 2009/0054721 A1* | 2/2009 | Martin | 600/4 |
| 2009/0171157 A1* | 7/2009 | Diederich et al. | 600/116 |
| 2009/0203987 A1* | 8/2009 | Steinmeyer et al. | 600/407 |
| 2010/0063496 A1* | 3/2010 | Trovato et al. | 606/34 |
| 2010/0069836 A1* | 3/2010 | Satake | 604/96.01 |
| 2010/0100092 A1* | 4/2010 | Turner et al. | 606/33 |
| 2010/0152519 A1* | 6/2010 | White et al. | 600/3 |
| 2010/0321192 A1* | 12/2010 | Brannan | 340/600 |
| 2011/0015628 A1* | 1/2011 | Dalal et al. | 606/34 |
| 2011/0017222 A1* | 1/2011 | Li et al. | 128/899 |
| 2011/0022044 A1* | 1/2011 | Garabedian et al. | 606/41 |

OTHER PUBLICATIONS

Dickler et al., "Treatment Volume and Dose Optimization of Mammosite Breast Brachytherapy Applicator," *Int. J. Radiation Oncology Biol. Phys.*, 59 (2): 469-474 (2004).

Dowlatshahi et al., "Laser Therapy for Small Breast Cancers," *The American Journal of Surgery*, 184: 359-363 (2002).

* cited by examiner

HIGH TEMPERATURE THERMAL THERAPY OF BREAST CANCER

This patent application is a non-provisional claiming priority under 35 U.S.C. §119(e) to U.S. Provisional Patent Application No. 60/808,064, filed May 24, 2006, and U.S. Provisional Patent Application No. 60/915,852, filed May 3, 2007, both of which applications are expressly incorporated herein by reference in their entirety. Methods and compositions are described for treating post-surgical breast cancer by applying heat to tissues surrounding a cavity remaining after surgical removal of cancerous tissue, thereby ablating remaining transformed cells and preventing metastasis of the transformed cells.

BACKGROUND OF THE INVENTION

Widespread annual screening mammography has resulted in detection of greater percentages of breast cancers measuring 1 cm in diameter. The diagnosis of malignancy and determination of the prognostic factors are typically made by image guided needle biopsy. The treatment of breast cancers involves a number of possible alternatives, including surgical removal, radiation therapy, chemotherapy, thermotherapy and combinations thereof. Breast tumors are surgically removed generally together with sentinel/regional lymph nodes.

Conventional techniques of post-operative treatment of residual tumors following gross removal of tumors include sequential or simultaneous administration of radiation and chemotherapy. Originally, radiation therapy involved whole breast irradiation. More recently partial irradiation of the lumpectomy cavity places an inflatable balloon in the space where the cancer was surgically removed to irradiate the surrounding tissue using an Iridium seed at the center of the balloon. This procedure typically requires multiple rounds of irradiation such as 15 minutes exposure, twice a day over a five day period. This procedure is also known as brachytherapy and has become the preferred alternative to whole breast irradiation. The rationale for this treatment is based upon the observation that over 80% of breast cancer recurrences appear within a radius of one centimeter from the initial tumor border. Success rates (reduced incidence of recurrence) using brachytherapy in breast cancer are considered to be similar to those of whole breast irradiation.

Breast cancer is a common malignancy in the United States and elsewhere in the world. Widespread screening mammography has resulted in detection of smaller tumors, in turn leading to breast saving operation i.e. lumpectomy and irradiation. Of late, partial irradiation of the affected site delivered through a radium source placed at the center of a balloon in one week is replacing the whole breast external beam irradiation given in six weeks. Although this approach shortens the treatment time and encourages more women to seek breast saving operation, it is still burdensome for the patient to carry a balloon in the breast for a week receiving treatment twice a day. Furthermore, the cost of the breast irradiation therapy remains high; an item which is part of the burgeoning healthcare budget.

Since the initial successes of brachytherapy, various intra-operative therapeutic procedures now utilize the cavity formerly occupied by the bulk of the tumor for placement of an inflatable device for subsequent tumor therapy, often in a combined modality (radiation and/or chemotherapy and/or hyperthermia together).

Radiation sources, e.g. a radium seed may be placed inside a balloon which is implanted into a breast of a patient. The balloon stays in place during the treatment period, e.g. for 10-15 days. When a patient returns for each treatment session (generally daily) the radiation source is inserted into the balloon for a period of time, perhaps twice a day, until the treatment period ends. This is inconvenient for the patient, and has the attendant risks and costs of radiation. Expenses include special facilities, radiation source and technical support.

Heat in balloons has been used to control uterine bleeding but not to destroy transformed cells. The uterus muscular tissue is very different type of tissue than breast and has a different construction than the breast (fatty tissue). Pressures of around 150 mm Hg are employed before the balloon device is activated, although pressure is generally not reported nor are descriptions of pathological effects on tissue of heat delivered in this manner.

SUMMARY

In contrast to post-surgical radiation therapy of breasts using balloon implants, methods and compositions are disclosed that use a balloon catheter with a balloon configured to conform to surgical cavities in the breast, balloons constructed to fill the cavity in the fatty breast tissue, using materials with sufficient rigidity and pressure to maintain shape of the balloon and to provide sufficient heat to destroy or inactivate cells in a specified thickness of tissue lining and surrounding the cavity.

Thermal therapy applied to breast cavities resulting from breast cancer surgery destroys transformed and potentially transformed tissue after a cancerous breast mass has been surgically removed.

Only one treatment is generally required, no special facilities are needed, and a CT scan can determine if cells in a specific area were destroyed or inactivated. Single treatment times of about 15 minutes are contemplated as adequate to remove, kill or inactivate transformed tissue in the vicinity of the post-surgical cavity. 7-15 minute cycles are contemplated.

Also described is a new electronic controller (algorithm) for the balloon catheter device. This allows control of temperature, time and pressure suitable for breast tissues. Also controlled is the relative size of the post-surgical cavity.

A method for reducing cancer recurrence by a thermal therapy includes:
 (a) administering a heated fluid into a cavity formed by surgical removal of cancer tissue including breast cancer; and
 (b) keeping the heated fluid in place until tissue surrounding the cavity is destroyed.

The temperature is about 60° C. in the cavity, 80-97° C. in the fluid in the cavity and is delivered for example by a catheter. A suitable heated fluid is dextrose.

A balloon containing the fluid is configured to conform to a cavity in a breast caused by removal of an undesirable growth, the configuration based on fatty tissue texture, thickness of the area around the cavity to be heated, rigidity of the balloon required to hold its form in a breast cavity, and pressure inside the balloon.

A method to control a balloon catheter used to place a balloon containing fluid inside a cavity in a breast caused by the removal of an undesirable growth, includes:
 (a) selecting a temperature in the range of 80°-97° C. to heat the fluid;
 (b) selecting a pressure in the range of 7-26 mm Hg; and
 (c) selecting time for lengths of cycles of heating.

DETAILED DESCRIPTION

A method for treating post-surgical breast cavities to ablate, kill, destroy, and/or sterilize any cancerous tissue that remains within a one centimeter radius of the cavity uses a balloon catheter commonly used in various surgical interventions and described for uterine applications in U.S. Pat. Nos. 4,949,718 and 6,139,570.

Partial breast irradiation (PBI) surrounding the lumpectomy cavity, utilizing a balloon with a radiation seed in its center (brachytherapy), has become an alternative to whole breast irradiation. The rationale for this new treatment is based upon the observation that over 80% of the breast cancer recurrences appear within one cm radius of the initial tumor border. Indeed the short term report of patients treated with brachytherapy using a Mammosite balloon indicates similar success rate as the whole breast irradiation. The depth of the targeted breast tissue destroyed by irradiation is one centimeter. A multi-center prospective clinical trial by NSABP is underway to test this concept.

Boiling water scalds the skin, burns the tongue and destroys bacteria. The mechanism of destruction is due to cell membrane disruption, disintegration of the intracellular organelles and the cell nucleus. The essence of the thermal therapy for post-lumpectomy cavity is that high heat (sub-boiling temperatures) penetrates the surrounding breast tissue to a depth comparable to radiation. The devitalized tissue is partially liquefied, which can be percutaneously aspirated, and partially removed by macrophages with the scar development comparable to any healing process.

A method for treating breast cancer reduces transformed tissue remaining in the breast after surgery. A post-surgical method directed to a cavity in a breast causes necrosis of the tissue surrounding the cavity. A method for high temperature thermotherapy of the tissue surrounding a removed breast cancer mass causes necrosis of remaining transformed tissue. Since no reliable in vivo method has been developed to determine if cells surrounding the cavity are transformed, the method targets the entire surface of the cavity, destroying cells uniformly within a targeted radius. This will eliminate any transformed cells or tissue and prevent the recurrence of breast cancer and/or metastases to other tissues.

The method of post-surgical transformed breast tissue requires a single application to ablate the transformed tissue and prevents recurrence of breast cancer or metastases to other tissues.

Thermotherapy is determined to be sufficient by itself to eliminate remaining cancerous cells in breast tissue after surgical removal. High temperature breast cancer removal using laser treatment has demonstrated that a temperature of 60 degree C. (140 degree F.) is sufficient to destroy breast tumors. Experience with such treatments has led to methods described herein whereby thermotherapy using a circulating fluid is sufficient to destroy post-surgical cavity tissue. The need for radioactive compounds, toxic chemicals, lasers, special fluids or gases is eliminated as heated 5% Dextrose in water (D5W) provides sufficient thermal transport and heat diffusion to the tissue surrounding the cavity and is capable of destroying tissue within a two centimeter radius of the balloon diameter. The need for multiple treatments, as is the case for chemotherapy or radiation therapy alone or in combination with low temperature thermotherapy is eliminated as the procedure works with a single treatment to ablate tissue surrounding the resection cavity. The liquid can be maintained at the correct temperature and maintained at that temperature with a heating coil commonly used in the balloon for the requisite time. Surface tissue damage is easily avoided by using a cold pack on the skin above the treatment area. Using the proper balloon or bladder will further allow the fluid to conform to non-uniform resection cavity and provide even heating in a uniform radius no matter the cavity shape.

Figure 1:
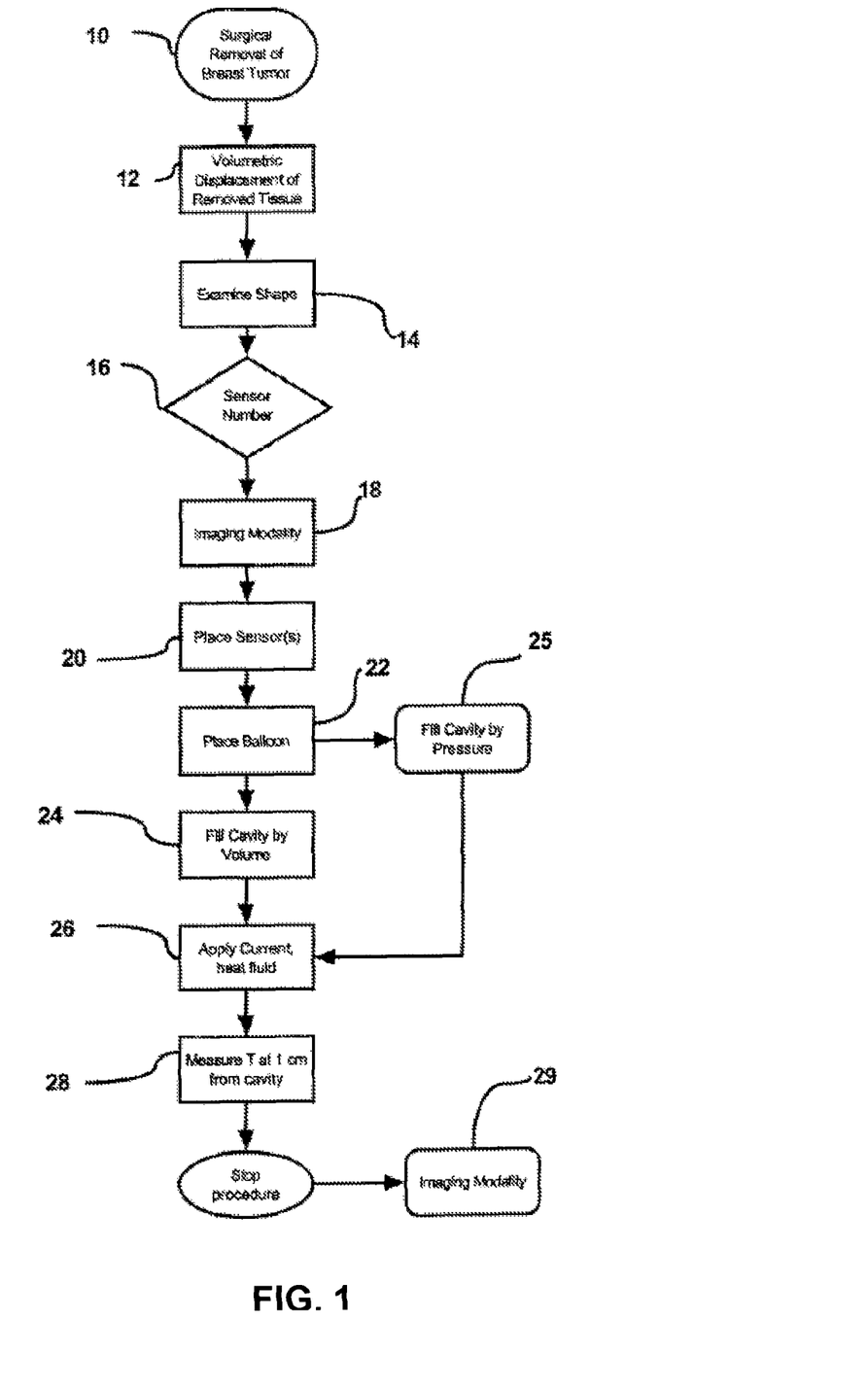
FIG. 1 shows a flow chart of the steps used in the high temperature thermotherapy treatment of breast tissue.

Referring to FIG. 1, after a cancerous (or precancerous) breast mass has been detected and removed via surgery 10, the removed tissue is examined for its shape and size. Volumetric displacement of the tissue 12 is used to determine the overall size of the mass. The mass is placed in a known amount of liquid such as water or saline and the change in the volume is determined. This change represents the overall volume of the mass and provides an estimate of the size of the cavity in the breast. Examining the shape 14 is done to determine if the removed mass is uniform in shape or has an unusual shape. The size and shape of the mass determines the number and placement of temperature sensors 16 used to identify the target temperature of tissue surrounding the cavity. Ultrasound or CT can also be used to determine the shape of the cavity or to verify the shape based on visual examination of the removed mass.

If the shape of the cancerous mass is uniformly spherical or oval shaped, one or two temperature sensors are used. Each sensor is placed 20 by the use of an imaging modality 18 to guide its placement. The sensor will monitor temperature in the tissue at a distance of one centimeter from the cavity. The imaging modality is ultrasound and is well known to those skilled in the art. An alternative imaging modality is computed tomography (CT) which is also well known to those skilled in the art. The chosen distance can range from one-half centimeter to two centimeters from the edge of the cavity with one centimeter being preferred.

With unusual, non-uniform shapes, multiple temperature sensors can be used and as many as five sensors on a single probe or up to five sensors on separate probes will be placed 20 at the selected distance and location around the cavity. Each sensor is placed at different positions around the irregularly shaped cavity, all located at a distance of one centimeter from the cavity edge. Alternatively a single probe with two to five temperature sensors is placed with the outer sensors placed at a distance of one centimeter from the cavity's edge and the inner sensors (if more than two) placed at a variable distance from the cavity's edge.

To place the thermal extra cavity sensor(s), the patient is positioned on a surgical table and ultrasound imaging is used to identify the location of the cavity. Alternatively, markers be used in combination with the ultrasound imaging to provide guidance for the probes. The shortest skin-to cavity route is preferably selected for placement of the thermal sensor(s) and the catheter and any intervening vessels are avoided during placement, although this is not critical for the post-surgical technique. Field anesthesia around the cavity is achieved with a long lasting local anesthetic, preferably 0.25% bupivacaine (approximately 50 cc); a single injection is sufficient for the procedure. An additional injection of anesthetic can be made if the patient begins to feel pain during the procedure.

The thermal needle sensor(s) made of surgical grade stainless steel (Omega Engineering, Stamford, Conn.) is placed through an incision in the breast and connected to its monitor. Alternative needle-type thermal sensors include the D-N12 series needle temperature probes made of stainless steel (Exacon Scientific, Copenhagen, Denmark) although any appropriate needle-type thermal sensor can be used for this purpose. Ultrasound is used to confirm proper position of the thermal sensor(s). CT can be used in place of ultrasound for this purpose.

After the thermal sensor(s) have been positioned, a second incision is made in the breast and a balloon catheter is inserted 22 so that the balloon is positioned completely inside the cavity. The catheter is guided using ultrasound imaging to follow a second skin to cavity route. In an alternate embodiment, reference points or markers can be used to assist the surgeon in guiding the catheter along the preferred route. A suitable catheter system is the Thermachoice™ II or Thermachoice™ III catheter system and controller (GyneCare WorldWide, Somerville, N.J.). Another catheter system contains sensors for measuring temperature and a heating element internal to the balloon. In another embodiment, the catheter system has a sensor for determining the pressure on the balloon when inflated. The balloon or bladder is strong enough to resist puncture under high temperature and pressure yet may be sufficiently thin to allow even heat flow from the liquid to the breast tissue. All sensor elements are connected to the monitor included with the catheter system.

After the temperature sensor needle(s) and the catheter have been placed, the balloon is filled with a liquid capable of providing even heat transfer from the balloon to the tissue. A suitable liquid is five percent dextrose in sterile water (D5W). Under the chosen imaging modality, the bladder is filled with the D5W until it has molded to the shape of the cavity. The predetermined volume of the cavity is used to determine the fill volume 24. Alternatively, the pressure sensor attached to the catheter system can be used to identify a pressure of 50 to 150 mmHg as the maximum fill 25, with a pressure of 100 mmHg, for example. Imaging using ultrasound of CT can be used to verify that the balloon has molded to the shape of the cavity.

After the balloon has been filled, a current is applied 26 to the heating element in the catheter and the fill liquid is heated to a temperature ranging from 80 degree C. to 97 degree C. (185 degree F. to 206.6 degree F.). After the temperature has reached the target, it is held constant until the temperature of the thermal sensor(s) placed at one centimeter from the cavity has reached 60 degree C. The thermal sensors are continuously monitored until this temperature has been achieved on all sensors. This is to destroy the tissue surrounding the cavity, including any transformed cells that were missed by the surgery.

After reaching 60 degree C., the current is turned off 28, the fill liquid is emptied from the catheter and the device is removed. The temperature probes are removed and the patient is discharged according to the standard operating procedures of the medical facility. A follow up examination 29 is performed to determine the efficacy of the procedure and specifically to verify that the targeted breast tissue has undergone necrosis. Imaging using contrast ultrasound or CT can reliably demonstrate the destruction of the tissue surrounding the cavity.

Figure 2:
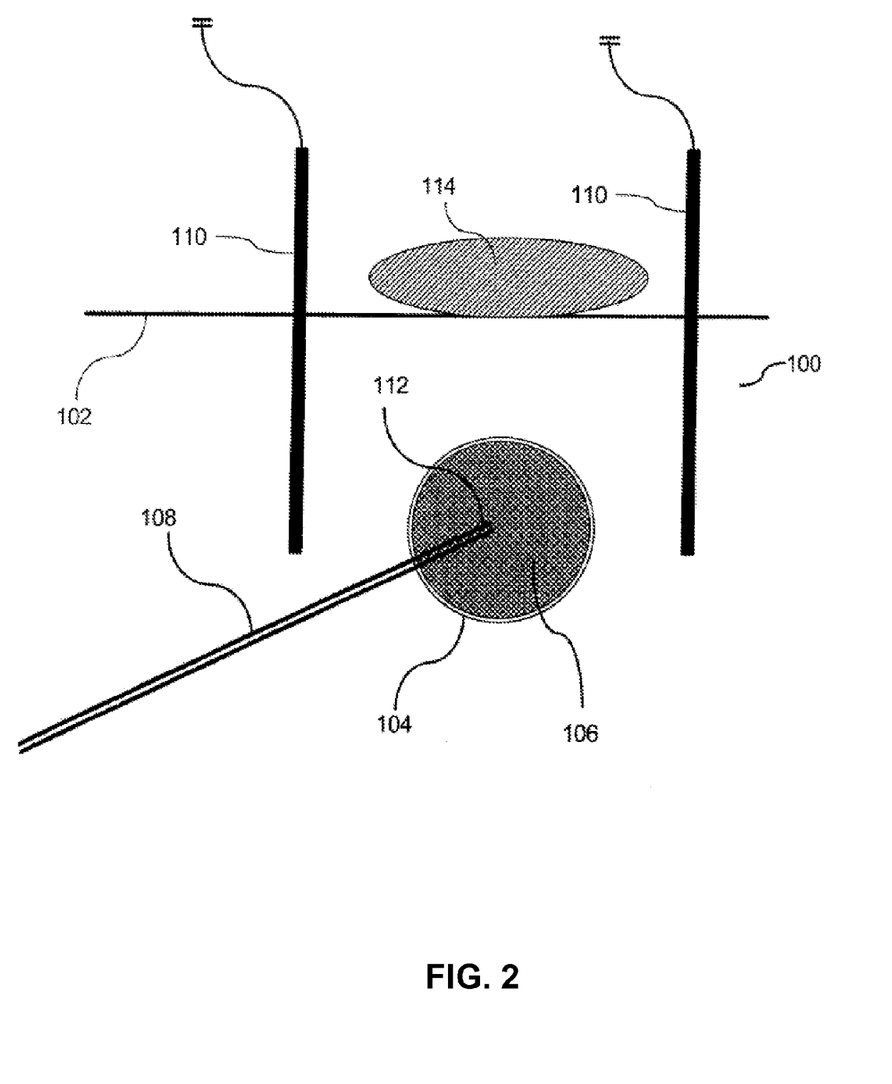
FIG. 2 shows a cross section cartoon of the catheter, balloon and sensors placed in and around a post-surgical breast cavity.
Figure 3:
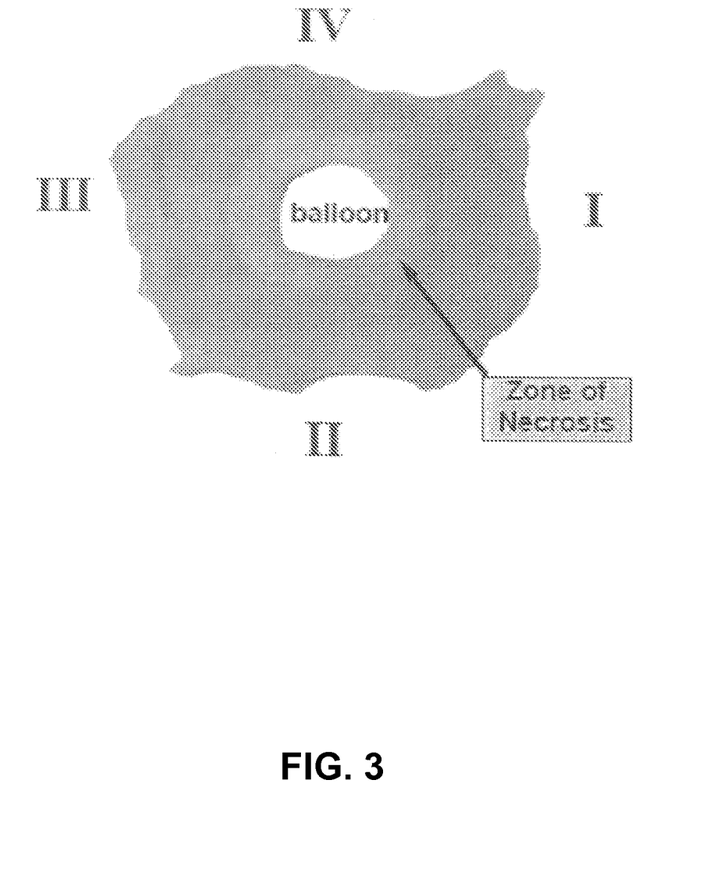
FIG. 3 is a diagrammatic section of a goat mammary gland with a balloon for thermal therapy and a zone for necrosis. Roman numerals indicate areas to be examined.
Figure 4:
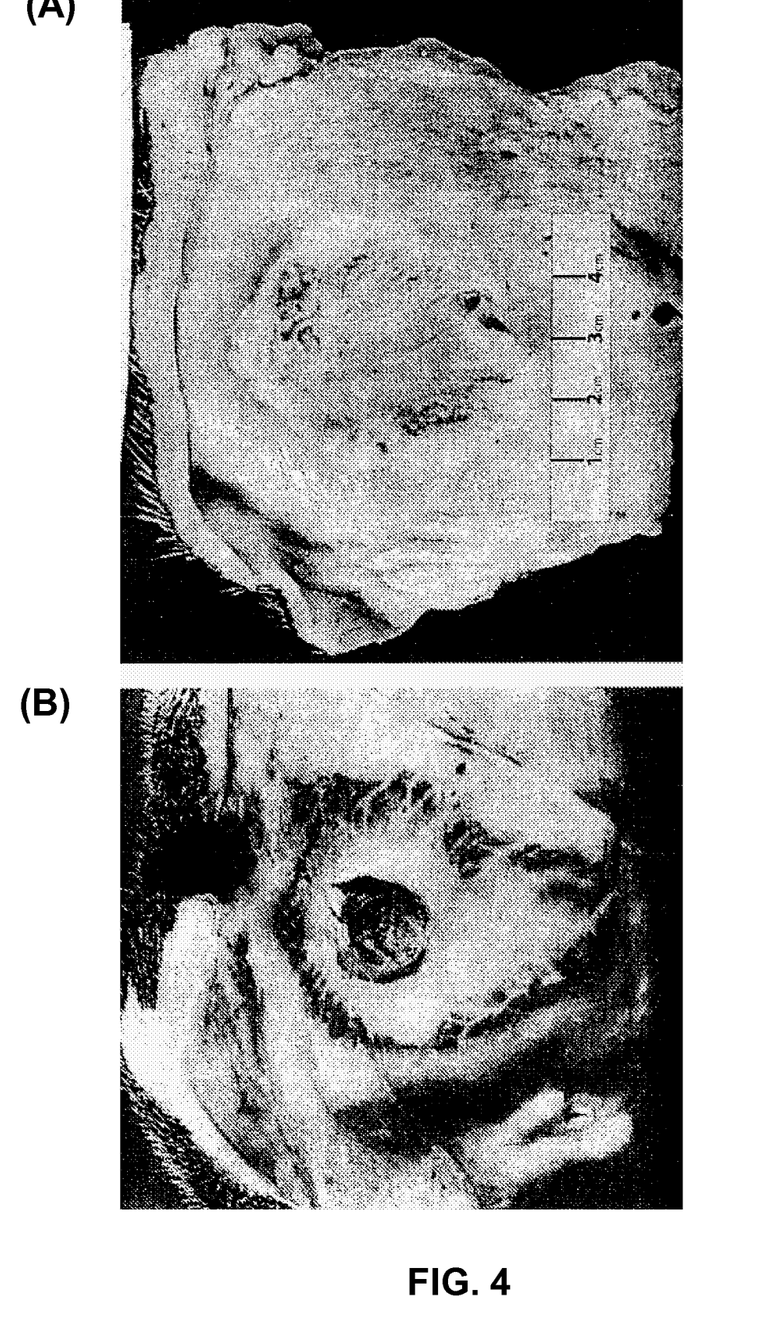
FIG. 4 shows pictures of goat mammary glands 5 and 20 days post-therapy.
Figure 5:
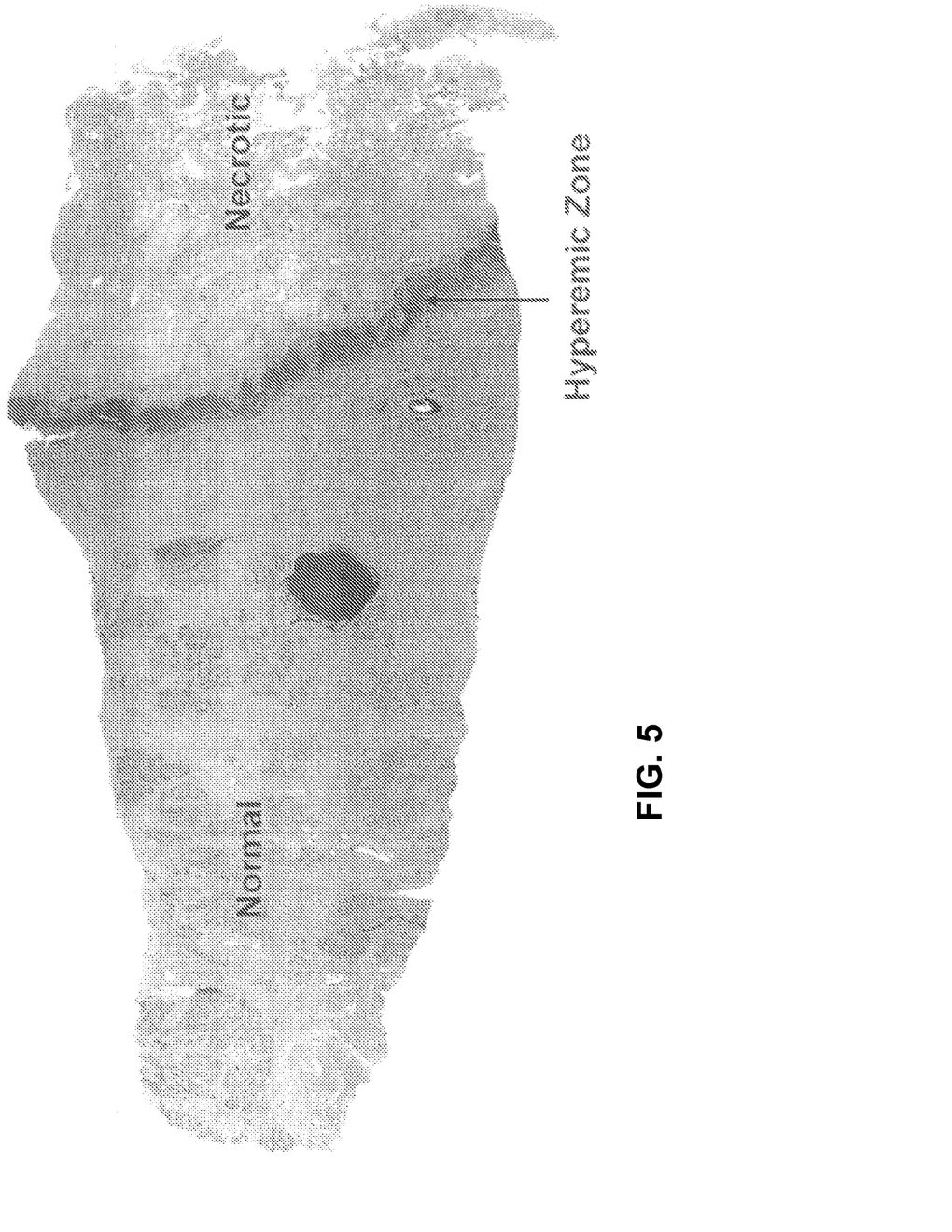
FIG. 5 shows a microscopic view of a goat mammary gland.
Figure 6:
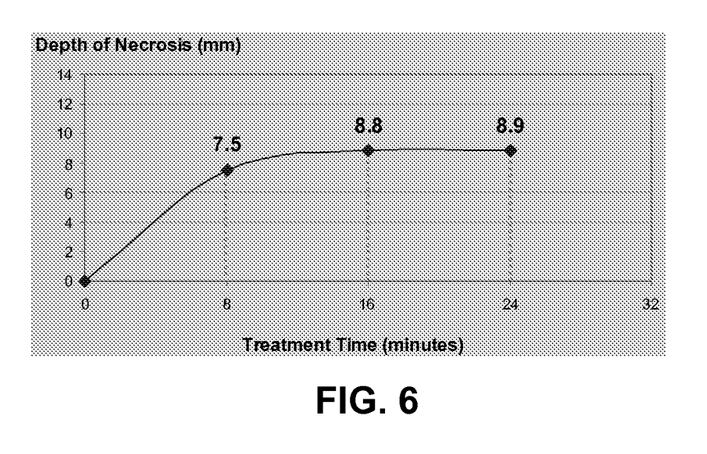
FIG. 6 shows the depth of necrosis of goat mammary gland upon thermal therapy.
Figure 7:
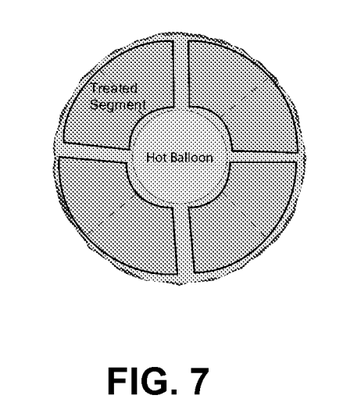
FIG. 7 is a diagram of a hot balloon and treated segments.

FIG. 2 provides a cross sectional view of the catheter and balloon in the cavity with two temperature sensors placed within the one centimeter radius of the cavity. In this case, the breast 100 with skin surface 102 shown has a cavity 104 located approximately one centimeter in depth from the skin 102. The catheter 108 and thermal balloon 106 have been placed via an incision in the skin 102 so the balloon 106 can be filled with D5W via a port (not shown) in the catheter 108 to fill the cavity 104. Pressure and temperature sensors (not shown) in the tip 112 of the catheter 108 are used as described to monitor the fill volume pressure and the temperature of the fill fluid. A heating element (not shown) located in the tip 112 of the catheter 108 is used to heat the fill fluid. Additional temperature sensors (110) are placed at one centimeter from the edge of the cavity 104. When the cavity 104 is near the skin 102 (defined as the cavity edge being within two centimeters of the skin), a cold pack 114 can optionally be used at the surface of the breast to regulate heating damage near the skin surface.

Controller

Figure 8:
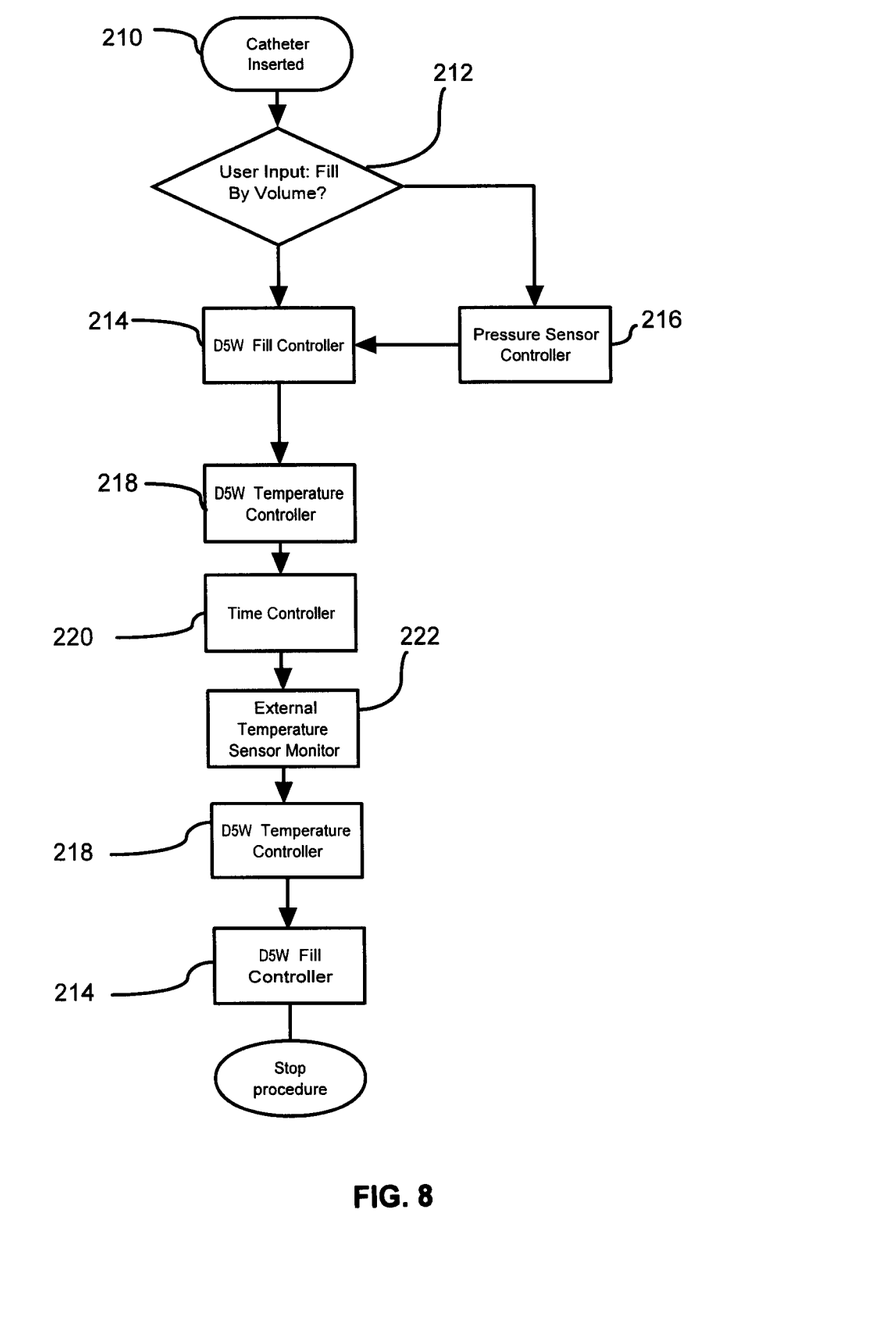
FIG. 8 is a flow chart of a controller for operation of a balloon catheter.

After the catheter has been inserted into the post-surgical cavity 210, the user inputs into the controller 212 instructions to fill the catheter by volume (for tissue masses that have uniform shape and have been measured using volumetric displacement as described) or to fill the catheter until a determined pressure has been obtained. If pressure is used to determine the fluid fill, a pressure sensor controller 216 attached to the pressure sensor in the catheter will be set to the desired pressure. The D5W fill controller 214 activates a pump to automatically fill the balloon according to the set parameters. The device then begins heating under the guidance of a D5W Temperature Controller 218 that is linked to the heating element and to the balloon temperature sensor in the catheter. Once the preferred temperature has been reached, a Time Controller 220 activates to monitor the time of the procedure. In the preferred method, one or more External Temperature Sensor Monitor(s) 222 is linked to the temperature sensors and monitors the desired temperature reached at a preferred distance from the balloon. The Time Controller 220 can be optionally set to override the External Temperature Sensor Monitors 222 and shut the procedure down if the procedure extends to a set override time point. Once the External Temperature Sensor Monitor(s) placed around the balloon has reached the desired temperature, the device signals the D5W Temperature Controller 218 to turn off the heating element and stop heating the fluid. The D5W Fill Controller 214 is then signaled to drain the balloon in preparation for its removal.

The targeted 1 cm zone of ablation, surrounding the lumpectomy cavity, may be achieved by heat propagated from a hot balloon placed in the lumpectomy cavity.

The balloon, inflated with 5% dextrose solution, is very similar to the Mammosite balloon except for the radium seed being replaced with an electrical element which heats the fluid to 87 degrees Celsius and maintains it at that level for a predetermined length of time. The device (Thermacare, by Ethicon) is clinically used for treatment of painful uterine dysfunction. It was selected for this project primarily to test the concept.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

EXAMPLES

Example 1

Thermal Ablation of the Goat Mammary Gland as a Model for Post-Lumpectomy Treatment of Breast Cancer Background:

Partial breast irradiation (PBI) post-lumpectomy for carcinoma deploying the Mammosite balloon catheter is practiced as alternative to the whole breast irradiation in selected patients. A one centimeter shell of targeted breast tissue surrounding the lumpectomy cavity may be effectively treated with a balloon inflated with hot fluid instead of irradiation.

Methods:

45-50 kilogram Nubian-Cross goats in post-partum phase were selected. Under endo-tracheal anesthesia, the mammary glands measuring 4-7 cm in diameter were visualized by ultrasound and 2-3 cc of the gland were excised for histological documentation and creation of a space for the balloon. A Thermacare deflated balloon (Ethicon) was inserted into the space and the incision was closed ensuring one cm thick tissue coverage. The balloon was inflated with 15-20 cc of 5% dextrose and pre-heated to 87° Celsius. At this temperature, mammary glands were treated for periods of 8, 16 and 24 minutes in successive animals that were euthanized 5 or 10-20 days later. The treated glands were excised, serially sectioned perpendicular to the axis of the catheter at 4-5 mm intervals and the necrotic thickness from the point of balloon contact outwards was microscopically measured at 4 points per each section. The mean value in mm of the necrosis was recorded against the treatment time in minutes. A total of 14 goats were utilized in this experiment; the first four were used for technical development. The reported data are based on the observations on the last 10 goats.

Eight animals were in the experimental group and two were used as controls.

| GOAT | amount of thermotherapy |
| --- | --- |
| #1 | 2 minutes |
| #2 | 4 minutes |
| #3 | 6 minutes |
| #4 | 8 minutes |
| #5 | 10 minutes |
| #6 | 12 minutes |
| #7 | 14 minutes |
| #8 | 16 minutes |
| #9 and 10 | control group |

To obtain an 80% chance of detecting a 20% difference in the size of tissue damage and necrosis between the samples from untreated and treated groups, at least 10 samples from each group are needed to achieve a 0.05 significance level in an ANOVA test or student t test. As the project stands now we will obtain 12 histologic samples from each animal at the given time interval.

Adult female goats weighing approximately 50 kilograms were used. Under sterile conditions, supine position and general endotacheal anesthesia by glycopyrrolate 0.005-0.01 mpk SQ; xylazine 0.03-0.05 mpk IV followed in 3 minutes by 2-3 mpk ketamine IV. The skin of the mammary area was prepared with Povidone iodine wash and alcohol rinse ×3. An elliptical 2×5 cm incision was made adjacent to the first nipple and 30-50 cc of the breast tissue (equivalent of a lumpectomy in patients with operable breast cancer) was removed using sharp dissection. The volume of the excised tissue was measured in a graduated cylinder containing saline and recorded. The deflated balloon is passed into the surgically created space through a small stab incision and was inflated with 30-50 cc of 5% dextrose. With ultrasound guidance the thermal sensor needles were inserted into the tissue 1 cm from the balloon surface. The incision is closed with 3/0 Proline. The balloon surface was at least 1 cm away from the skin, whose temperature will be monitored and if that exceeds 40 Celsius, the skin was cooled with a cold pack.

Thermal Therapy

The fluid in the balloon was heated to 95 Celsius using the balloon device. The actual treatment commences after the temperature reaches 95° C. and finished promptly at 2 minute intervals. The balloon was deflated and was removed from the animal. Sterile dressing with an adhesive was applied to the incisions. An identical operation was performed on the second mammary gland of the goat at the next time interval.

The animal was then awakened, extubated and transferred to the recovery room. Over the next 48 hours, each goat was given antibiotic naxcel at 1.1 mg/kg body weight once a day and carprofen at 2-4 mg/kg im.

Eight animals were tested, starting at 2 minutes for the first one; the duration of the heat treatment was incrementally increased at 2 minutes. Thus the eighth goat was treated for 16 minutes. At each stage, the treatment will be given to 2 animals in both mammary glands for a total of 4 observations. Forty eight hours later, the animals were euthanized and the thermally targeted tissue excised for pathologic examination. The depth of necrosis in millimeters, as defined by a hyperemic zone between viable and devitalized tissue, was measured. Sections of the mammary tissue were examined by pathology. A total of ten goats—eight for testing, and two for controls—were needed.

Analysis of the data includes pathologically measuring the thickness in millimeters of tissue necrosis versus the duration of time in the thermally treated mammary tissue presented as a graph and the time it takes to reach the maximal effect of heat on the surrounding mammary tissue of the goat (plateauing of the thermal curve). This was presented as a graph.

The device: "Thermacare", manufactured by Ethicon, is programmed to operate at 87 degree Celsius and 150 mm Hg for 8 minute cycles. The inflexibility of the program did not allow the operator to collect data for the first 8 minutes to plot the early portion of the thermal curve to determine the necrosis.

The balloon pressure is fixed to reach 150 mm Hg before the ablation process is commenced. This is appropriate for a muscular uterine application and not for the future breast lumpectomy space where a pressure of 20-40 mm Hg is the average figure noted by the inflated Mammosite balloon.

The data points derived for the three temperature observations of 8, 16 and 24 minutes had wide range of 3 to 20 mm ablation (necrotic depth) from the point of contact with the balloon sections of the thermally treated glands were taken perpendicular to the long axis of the balloon and not radially from the point of balloon contact with the tissue to represent circumferential heat spread. Tighter points will demonstrate more uniform heat propagation unless there is a significant heat sink in the area such as an artery.

Results:

Acute circumferential necrosis of the mammary gland was noted extending from the point of balloon contact with the mammary gland outwards. The data were taken from 20 thermally treated mammary glands in 10 goats. The mean necrosis depth (mm) was tabulated against time in minutes. The depth of necrosis ranged from 3-20 mm with the mean of 7.5, 8.8 and 8.9 mm for 8, 16, 24 minutes of treatment time respectively. The programmatic restrictions (electronic controller) of the device such as the time cycles and the high balloon pressure designed for endometrial therapy precluded optimal heat delivery to the mammary gland. Nevertheless, 20 mm zone of necrosis was noted in several instances in different animals.

Conclusion

A model for breast heat therapy is the goat mammary gland. The thermal methods and compositions simulating lumpectomy in human patients, predicts success. Clinical trials will use heat therapy first, and a CT scan to check for tissue damages surrounding the surgical cavity in the breasts, prior to proceeding with standard radiation therapy.

TABLE

Results of Heat Therapy, Goat Mammary Glands

| Treatment Time (mins) | Number of Sections | Mean (Range) Necrosis in mm |
|---|---|---|
| 8 | 81 | 7.5 (3-20) |
| 16 | 69 | 8.8 (4-15) |
| 24 | 59 | 8.9 (4-17) |

Example 2

Necrosis in a Cow Udder by Thermal Therapy

Fresh, resected bovine udders were obtained from a local slaughterhouse and tested ex vivo using the thermal therapy system. A deflated balloon was passed into the tissue through a small stab incision and was inflated with 30-50 cc of 5% dextrose in water. Thermal sensor needles were inserted into the tissue 1 cm from the balloon surface. The fluid in the balloon was heated to 95 Celsius. The actual treatment commences after the temperature reaches 95° C. and finished promptly at 2 minute intervals. After the temperature of the sensors reached 60° Celsius, the heating element was turned off and the fluid removed. The deflated balloon was then removed from the tissue. A deep incision was made in the tissue to the point of contact between the balloon and the tissue and the cavity was examined visually and under the microscope.

Analysis of the data included measuring the diameter of the cavity and measuring the thickness of tissue necrosis versus the duration of time in the thermally treated mammary tissue. Pathological examination was performed to examine necrotized versus normal tissue. Acute circumferential necrosis of the tissue was noted extending from the point of balloon contact with the mammary gland outwards.

PUBLICATIONS CITED

Dickler et al (Intl Jrnl Radiation Oncology & Biological Physics, Vol 59, No 2 pps 469-474)

Dowlatshahi et al, J. Am Surgery, vol 184 pps 359-363

I claim:

1. A method to kill cells surrounding a cavity with heated fluid using a balloon catheter wherein the cavity is caused by the removal of an undesirable growth and wherein the cavity may have various shapes, the method comprising:
   (a) conforming the balloon to the shape of the cavity by determining the volume of the cavity and providing sufficient fluid to fill the cavity based on the volume;
   (b) reaching a temperature in the range of 80°-97° C. in the fluid to achieve a temperature in tissues surrounding the cavity that kills cells; and
   (c) spacing a plurality of temperature sensors from the cavity, wherein a number and placement of the temperature sensors are selected based on a shape and a size of the cavity.

2. The method of claim 1, further including monitoring a temperature of the tissue surrounding the cavity.

* * * * *